(12) United States Patent
Lee (10) Patent No.: US 9,017,950 B2
(45) Date of Patent: Apr. 28, 2015

(54) METHOD FOR ENHANCING ENZYME ASSAYS

(75) Inventor: Ji Hoon Lee, Gaithersburg, MD (US)

(73) Assignee: Luminescent MD, LLCMD (US)

( * ) Notice: Subject to any disclaimer, the term of this patent is extended or adjusted under 35 U.S.C. 154(b) by 80 days.

(21) Appl. No.: 13/422,650

(22) Filed: Mar. 16, 2012

(65) Prior Publication Data

US 2012/0237957 A1    Sep. 20, 2012

Related U.S. Application Data

(60) Provisional application No. 61/454,026, filed on Mar. 18, 2011.

(51) Int. Cl.
| | |
|---|---|
| *G01N 33/53* | (2006.01) |
| *G01N 33/533* | (2006.01) |
| *C12Q 1/28* | (2006.01) |
| *G01N 33/535* | (2006.01) |
| *G01N 33/542* | (2006.01) |

(52) U.S. Cl.
CPC .............. *G01N 33/5306* (2013.01); *C12Q 1/28* (2013.01); *G01N 33/535* (2013.01); *G01N 33/542* (2013.01)

(58) Field of Classification Search
None
See application file for complete search history.

(56) References Cited

U.S. PATENT DOCUMENTS

| | | | | |
|---|---|---|---|---|
| 4,521,511 | A * | 6/1985 | Stout | 435/28 |
| 5,736,320 | A * | 4/1998 | Schlederer et al. | 435/5 |
| 7,141,677 | B2 * | 11/2006 | Lee et al. | 548/334.1 |
| 8,492,101 | B2 * | 7/2013 | Lee | 435/7.1 |
| 2003/0073150 | A1 * | 4/2003 | Woerner et al. | 435/7.92 |

OTHER PUBLICATIONS

Luo et al., "The study of a chemiluminescence immunoassay using the peroxyoxalate chemiluminescent reaction and its application," Talanta, 2007, vol. 72, issue 4, pp. 1293-1297.*

Lee et al., "Fast peroxyoxalate chemiluminescence for minimized analytical separation systems," Chem. Commun., 2003, issue 2, pp. 270-271.*

* cited by examiner

*Primary Examiner* — Galina Yakovleva
(74) *Attorney, Agent, or Firm* — Birch, Stewart, Kolasch & Birch, LLP (57) ABSTRACT

Additives capable of controlling the reaction rate between substrate and enzyme to form a dye in enzyme assays with absorbance, chemiluminescence, and fluorescence are effective tools for optimizing enzyme assays. A dye can be formed rapidly from the reaction between enzyme and substrate in the presence of a catalyst. Using relatively high concentration of dye formed from the rapid reaction, trace levels of analytical materials can be quantified using absorbance, chemiluminecence and fluorescence detection. A dye can be formed from a relatively slow reaction between enzyme and substrate in the presence of a surfactant such as Triton X-100 and β-cyclodextrin. Using relatively low concentration of dye from the slow reaction, a high concentration of analytical material can be quantified without any dilution using absorbance, chemiluminescence, and fluorescence.

1 Claim, 6 Drawing Sheets

METHOD FOR ENHANCING ENZYME ASSAYS

CROSS REFERENCE TO RELATED APPLICATIONS

This application claims the benefit of U.S. Patent Application Ser. No. 61/454,026, filed Mar. 18, 2011.

FIELD OF INVENTION

This invention involves enzyme assays for quantifying biomarkers and toxic materials using various detection methods such as absorbance, chemiluminescence and fluorescence.

BACKGROUND

Enzyme assay methods are widely applied in various fields such as biochemistry, clinical chemistry, homeland security, molecular biology, pathology, and toxicology. The sensitivity of enzyme assays capable of sensing analyte existing in a small volume of a sample is dependent on various factors such as the components as well as concentration of buffer solution, incubation time, the reactivity between enzyme and substrate, temperature, and detection method (e.g., absorbance, chemiluminescence, fluorescence). It is possible to rapidly quantify trace levels of analytical materials when these factors are optimized.

The condition of each factor can be optimized independently, but these factors interact in a complementary manner to enhance the accuracy, precision, reproducibility, and sensitivity. For example, it is well-known that chemiluminescence detection is more sensitive than absorbance and fluorescence, which have relatively high background noise. An enzyme assay with chemiluminescence detection is faster than those with absorbance and fluorescence because the incubation time of the former is shorter than that of the latter. Thus, it is desirable to be able to optimize enzyme assay methods to more easily and rapidly detect low-level concentrations of analytes as well as to be able to quantify higher concentrations.

SUMMARY

The present invention provides additives (e.g., catalyst, surfactant) capable of controlling the reaction rate between substrate and enzyme to form a dye in enzyme assays with absorbance, chemiluminescence, and fluorescence. A dye can be formed rapidly from the reaction between enzyme and substrate in the presence of a catalyst such as p-Iodophenol and 4-(1,2,4-triazol-1-yl) phenol. Using relatively high concentration of dye formed from the rapid reaction, trace levels of analytical materials can be quantified using absorbance, chemiluminecence and fluorescence detection. A dye can be formed from the relatively slow reaction between enzyme and substrate in the presence of a surfactant such as Triton® X-100 surfactant and β-cyclodextrin. Using relatively low concentration of dye from the slow reaction, a high concentration of analytical material can be quantified without any dilution using absorbance, chemiluminescence, and fluorescence.

DETAILED DESCRIPTION AND EXAMPLES

The present invention involves the development of additives (e.g., catalyst, surfactant) to optimize enzyme assays such as enzyme immunoassays as well as conventional analytical methods capable of rapidly sensing various biological materials (e.g., glucose, choline, acetylcholine, cholesterol).

Catalysts used in enzyme assays can include p-Iodophenol, 4-(Dimethylamino) pyridine, 4-Morpholinopyridine, P-Coumaric acid, 4-Aminopyridine, 4-(1,2,4-triazol-1-yl) phenol, and 4-(1-imidazolyl) phenol.

Surfactants used in enzyme assays can include Triton® X-100, Triton® X-114, Triton® X-405, Triton® X-705, α-cyclodextrin, (2-Hydroxypropyl)-β-cyclodetrin, β-cyclodextrin, Carboxymethyl-β-Cyclodextrin, Carbomethyl-β-cyclodextrin sodium salt, γ-cyclodextrin, Sodium dodecyl sulfate, Hexadecyltrimethylammonium bromide, and Hexadecyltrimethylammonium chloride.

Enzymes used in enzyme immunoassays with absorbance, chemiluminescence, and fluorescence can include acetylcholinesterase (AChE), alkaline phosphatase (ALP), and horseradish peroxidase (HRP).

Enzymes used in conventional analytical methods can be AChE, HRP and various enzymes (e.g., glucose oxidase, choline oxidase, cholesterol oxidase) used for the quantification of specific biological material such as glucose, choline, acetylcholine, cholesterol.

Substrates used in enzyme immunoassay with absorbance detection include p-Nitrophenyl Phosphate, Disodium Salt (PNPP), 2,2'-Azinobis (3-ethylbenzothiazoline-6-sulfonic acid) diammonium salt (ABTS), o-phenylenediamine dihydrochloride (OPD), and 3,3',5,5'-tetramethylbenzidine (TMB).

Substrates used in enzyme assay with fluorescence detection can include Amplex® Red reagent, 2,3-diaminophenazine (DAPN), fluorescein diphosphate (FDP), 4-methyl umbelliferyl phosphate (MUP), and 3-O-methyl fluorescein phosphate.

Substrates used in enzyme assay with luminol chemiluminescence detection include luminol derivatives such as luminol and isoluminol.

Substrates used in enzyme assay with 1,2-dioxetane chemiluminescence detection include 1,2-dioxetane derivatives.

Substrates used in enzyme assay with 1,1'-oxalyldiimidazole (ODI) derivative chemiluminescence detection include Amplex® Red reagent, 2,3-diaminophenazine (DAPN), fluorescein diphosphate (FDP), 4-methyl umbelliferyl phosphate (MUP), and 3-O-methyl fluorescein phosphate.

Substrates used in enzyme assay with 1,1'-oxalyldisodium benzoate (ODB) derivative chemiluminescence detection include Amplex® Red reagent, 2,3-diaminophenazine (DAPN), fluorescein diphosphate (FDP), 4-methyl umbelliferyl phosphate (MUP), and 3-O-methyl fluorescein phosphate.

ODI derivatives include 1,1'-Oxalyldiimidazole; 1,1'-Oxalyldi-2-methyl-imidazole (OD2MI); 1,1'-Oxalyldi-2-ethyl-imidazole (OD2EI); and 1,1'-Oxalyldi-4-methyl-imidazole (OD4MI).

ODB derivatives include 1,1'-oxalyldi-2-sodiumbenzoate (OD2B) and 1,1'-oxalyldi-4-sodiumbenzoate (OD4B).

Reagents and Kits

Chemicals: Bis(2,4,6-trichlorophenyl)oxalate (TCPO), Imidazole (ImH), 2-Methylimidazole (2MImH), 2-Ethylimidazole (2EImH), 4-Methylimidazole (4MImH), o-phenylenediamine (OPDA), 30% Hydrogen peroxide ($H_2O_2$), 4-Hydroxybenzoic acid sodium salt, $MgCl_2$, and $CaCl_2$ were purchased from Sigma-Aldrich. Ethyl acetate (HPLC grade), Isopropyl alcohol (HPLC grade), deionized water (LC-MS grade), and Dimethylsulfoxide (DMSO) were purchased from EMD chemicals. Amplex® Red reagent was purchased from Biotium. Fluorescein diphosphate, tetraammonium salt (FDP) and 4-methyl umbelliferyl phosphate (MUP) were purchased from AnaSpec. 0.1M sodium phosphate EDTA buffer solution (pH 7.4) was purchased from Teknova. Sterile human serum was purchased from Rockland Immunochemicals. p-Iodophenol, 4-(Dimethylamino) pyridine, 4-Morpholinopyridine, P-Coumaric acid, and 4-(1,2,4-triazol-1-yl) phenol were purchased from Sigma. Acetylcholinesterase (AChE), alkaline phosphatase (ALP), and horseradish peroxidase (HRP) were purchased from Sigma. Triton® X-100, Triton® X-114, Triton® X-405, Triton® X-705 surfactants, α-cyclodextrin, (2-Hydroxypropyl)-β-cyclodetrin, β-cyclodextrin, Carboxymethyl-β-cyclodextrin, Carbomethyl-β-cyclodextrin sodium salt, γ-cyclodextrin, Sodium dodecyl sulfate, Hexadecyltrimethylammonium bromide, and Hexadecyltrimethylammonium chloride were purchased from Sigma-Aldrich. Bisphenol A (BPA) was purchased from Aldrich. BPA Elisa Kit was purchased from Beacon Analytical System, Inc. Alphafetoprotein (AFP), Prostate Specific Antigen (PSA), and Carcinoembryonic Antigen (CEA) as one of AccuLite® CLIA kits applied with luminol CL detection were purchased from Monobind. 1,2-dioxetane and luminol CL reagents prepared under optimum condition were purchased from KPL.

Instruments

In order to measure light under various chemiluminescence enzyme assay conditions, Luminoskan Ascent with two dispensers (Thermo Scientific) and LB 9507 Luminometer with two dispensers (Berthold Technologies) were used.

In order to measure absorbance and fluorescence under various enzyme assay conditions, Infinite M1000 well-plate reader (TECAN) was used.

Example 1

Catalysts Capable of Enhancing the Sensitivity of Enzyme Assay a. Effects of Catalysts Added in the Reaction Between $H_2O_7$ and Substrate in the Presence of HRP 0.25 mM of six different catalysts (p-Iodophenol, 4-(Dimethylamino) pyridine, 4-Morpholinopyridine, p-Coumaric acid, 4-aminopyridine, 4-(1,2,4-triazol-1-yl) phenol) were prepared in Tris-HCl buffer solution (pH 8.5).

2.0 μM Amplex® Red reagent in deionized water was prepared as a substrate for ODI derivative CL detection.

0.04 U/ml HRP containing 2.0 mM $H_2O_2$ was prepared in Tris-HCl buffer solution (pH 8.5).

1,1'-Oxalyldi-4-methyl-imidazole (OD4MI), one of ODI derivatives formed from the reaction between 5.0 μM TCPO, and 10.0 μM 4-Methylimidazole (4MImH) in Ethyl acetate. 100 mM $H_2O_2$ was prepared in Isopropyl alcohol.

Procedure

5. Mix and incubate 0.8 ml of Amplex® Red reagent (or deionized water), 0.1 ml of catalyst (or Tris-HCl buffer solution), and 0.1 ml of the mixture of HRP and $H_2O_2$ for 90 seconds in a 1.5 ml-centrifuge tube at room temperature.
6. Pipette 10 μl of working solution into the assigned test tube (12×75 mm) or strip well.
7. Insert the test tube into a luminometer or the strip well into a microplate luminometer.
8. Read CL emitted when OD4MI and $H_2O_2$ are added into the test tube or strip well through two dispensers.

Figure 1:
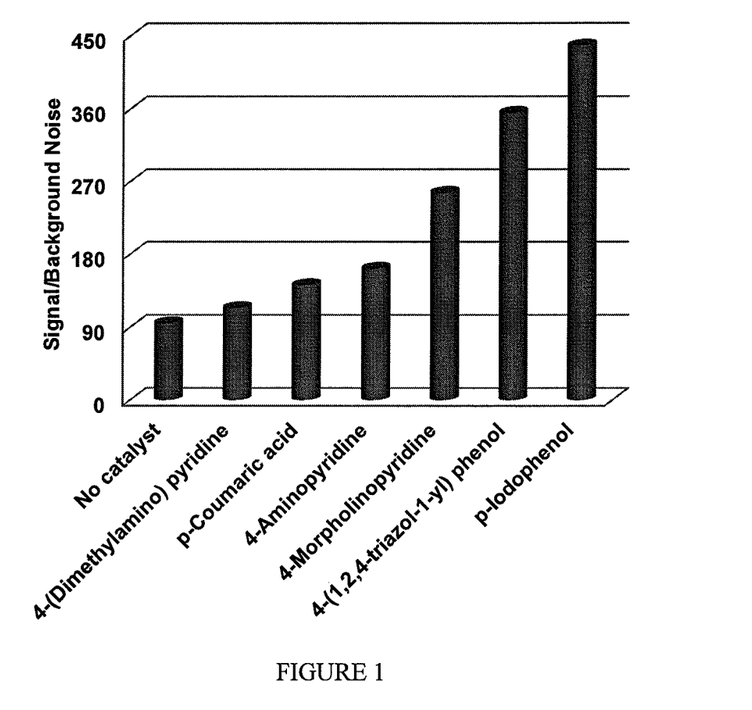
FIG. 1 shows the signal to background noise in the absence or presence of catalyst using ODI derivative CL detection.

FIG. 1 indicates that various catalysts can be applied as a signal enhancer in the enzyme reaction of Amplex® Red reagent and $H_2O_2$ in the presence of HRP. Also, the reaction rate of the enzyme reaction in the presence of catalyst is faster than that in the absence of catalyst. Based on the results of FIG. 1, it is possible to propose enzyme reaction mechanisms as shown FIGS. 1A and 1B.

Figure 1A:
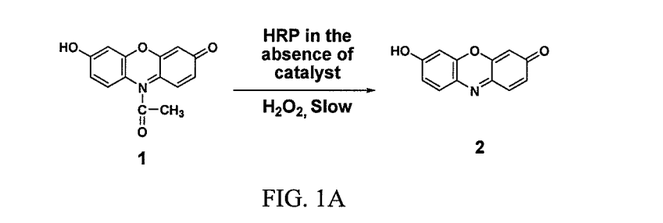

FIG. 1A shows a slow enzyme reaction in the absence of catalyst for the low yield of resorufin. 1. Amplex® Red reagent, 2. Resorufin.

Figure 1B:
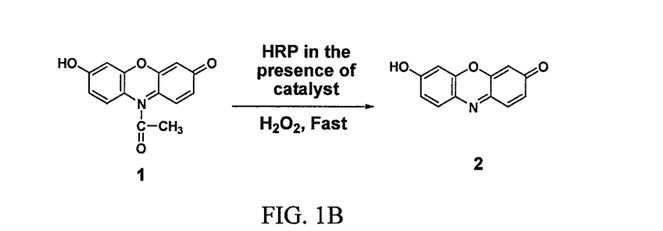

FIG. 1B shows a rapid enzyme reaction in the presence of catalyst for the high yield of resorufin. 1. Amplex® Red reagent, 2. resorufin In addition, fluorescence of resorufin formed from the reactions shown in FIGS. 1A and 1B. The ratios of signal and background noise in the absence and presence of catalyst observed using fluorescence detection were similar to those shown in FIG. 1.

B. Quantification of PSA Using PSA Detection Antibody-HRP Conjugate and ODI Derivative CL Detection in the Presence of 4-Iodophenol and 4-(1,2,4-Triazol-1-Yl) Phenol Preparation AccuLite® CLIA kit capable of quantifying PSA with luminol CL detection was used to develop new CLEIA method using ODI derivative CL detection. The kit is composed of 96 strip wells coated with monoclonal PSA primary antibody, PSA detection antibody-HRP conjugate, luminol as a substrate, reaction buffer, and washing buffer.

8 different PSA serum samples (0, 0.5, 1, 2, 5, 10, 25, 50 ng/ml), components of AccuLite® CLIA kit, were used as standard samples.

2.0 μM Amplex® Red reagent and 0.2 mM $H_2O_2$ in deionized water were prepared as described in Example 1 (A).

0.5 mM 4-Iodophenol was prepared in Tris-HCl buffer solution (pH 8.5).

2.0 mM 4-(1,2,4-triazol-1-yl) phenol was prepared in Tris-HCl buffer solution (pH 8.5).

0.8 ml of aqueous solution containing Amplex® Red reagent (2.0 μM) and $H_2O_2$ (0.2 mM) was mixed with 0.2 ml of 4-Iodophenol (or 2.0 mM 4-(1,2,4-triazol-1-yl) phenol).

OD4MI was formed from the reaction between 5.0 μM TCPO and 10.0 μM 4-Methylimidazole (4MImH) in Ethyl acetate. 100 mM $H_2O_2$ was prepared in Isopropyl alcohol.

Procedure

12. Pipette 25 µl of PSA standard or test sample into a strip well.
13. Add 100 µl of PSA detection antibody-HRP conjugate to the strip well
14. Swirl the strip wells for 20 seconds.
15. Incubate for 20 minutes at 37° C.
16. Discard the contents of each strip wells.
17. Wash each plate with 300 µl washing buffer. Repeat four additional times.
18. Add 100 µl working solution containing 2.0 µM Amplex® Red reagent and 0.2 mM $H_2O_2$ to each strip well.
19. Incubate the strip-well containing Amplex® Red reagent, $H_2O_2$, and 4-Iodophenol (or 2.0 mM 4-(1,2,4-triazol-1-yl) phenol) for 5.0 minutes at room temperature (21~23° C.) in the dark.
20. Pipette 10 µl of working solution into the assigned test tube (12×75 mm).
21. Insert the test tube into a luminometer or the strip well into a microplate luminometer.
22. Read (integration time: 0.5 seconds) emitted CL for 0.5 seconds when OD4MI and $H_2O_2$ are added into the test tube or strip well through two dispensers.

Figure 2:
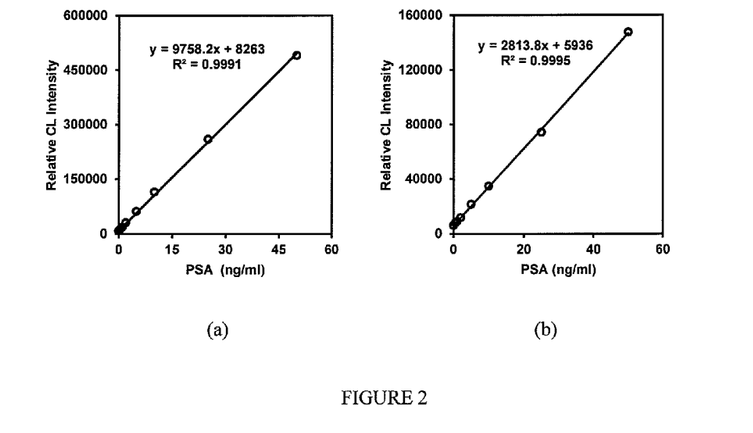
FIG. 2 shows a calibration curve for quantifying PSA in OD4MI CLEIA in the presence of (a) 4-Iodophenol and (b) 4-(1,2,4-triazol-1-yl) phenol.

As shown in FIG. 2, the calibration curve having good $R^2$ was obtained under wide concentration ranges of PSA. The dynamic range (0~50 ng/ml) obtained in the presence of 4-Iodophenol was the same as that in the presence of 4-(1,2,4-triazol-1-yl) phenol. However, the limit of detection (LOD, the measurement of zero dose+3 standard deviations=0.03 ng/ml) in the presence of 4-Iodophenol was about 2 times lower than that (0.07 ng/ml) in the presence of 4-(1,2,4-triazol-1-yl) phenol. In addition, the LOD in the presence of 4-Iodophenol or 4-(1,2,4-triazol-1-yl) phenol was about 20 or 10 times lower than that in the absence of catalyst.

Example 2

Surfactants Capable of Extending the Dynamic Range of Enzyme Assay

A. Effects of Surfactants Added in the Reaction Between $H_2O_2$ and Substrate in the Presence of HRP Various concentrations (0.5, 1.0, and 1.5%) of Triton® X surfactant derivatives (Triton® X-100, Triton® X-114, Triton® X-405, and Triton® X-705) were prepared in Tris-HCl buffer solution (pH 8.5).

Various surfactants (e.g., (2-Hydroxypropyl)-β-cyclodetrin, β-cyclodextrin, Carboxymethyl-β-cyclodextrin, Carbomethyl-β-cyclodextrin sodium salt, γ-cyclodextrin, Sodium dodecyl sulfate, Hexadecyltrimethylammonium bromide, Hexadecyltrimethylammonium chloride) of critical micelle concentration (CMC) were prepared in Tris-HCl buffer solution (pH 8.5).

As a substrate for ODI derivative CL detection, 2.0 µM Amplex® Red reagent in deionized water was prepared.

Various concentrations (0~0.1 U/ml) of HRP containing 2.0 mM $H_2O_2$ was prepared in Tris-HCl buffer solution (pH 8.5).

1,1'-Oxalyldi-4-methyl-imidazole (OD4MI), one of ODI derivatives was formed from the reaction between 5.0 µM TCPO, and 10.0 µM 4-Methylimidazole (4MImH) in Ethyl acetate. 100 mM $H_2O_2$ was prepared in Isopropyl alcohol.
Procedure
5. Mix and incubate 0.8 ml of Amplex® Red reagent (or deionized water), 0.1 ml of surfactant, one of various surfactants used in this research, and 0.1 ml of HRP containing $H_2O_2$ for 10 minutes in a 1.5 ml-centrifuge tube at room temperature.
6. Pipette 10 µl of working solution into the assigned test tube (12×75 mm) or strip well.
7. Insert the test tube into a luminometer or the strip well into a microplate luminometer.
8. Read CL emitted when OD4MI and $H_2O_2$ are added into the test tube or strip well through two dispensers.

Figure 3:
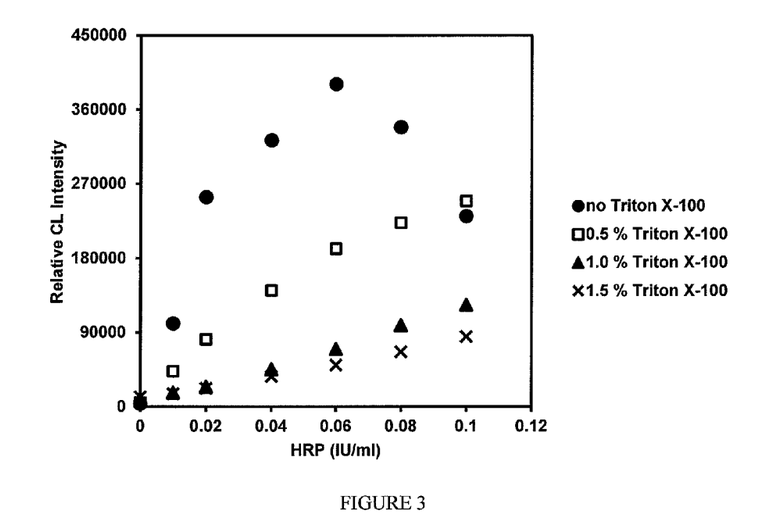
FIG. 3 shows the effect of Triton® X-100 surfactant in enzyme assay with OD4MI CL detection to quantify HRP at room temperature.
Figure 4:
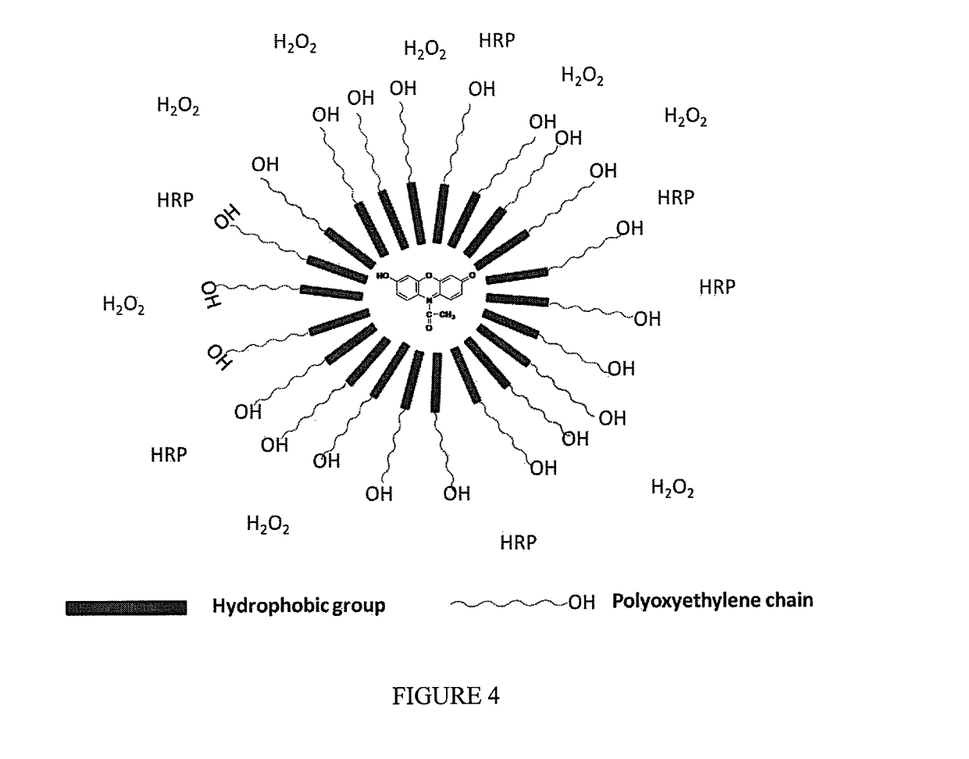
FIG. 4 shows the interference effect of Triton® X-100 surfactant in the reaction of Amplex® Red reagent and $H_2O_2$ in the presence of HRP.

The results shown in FIG. 3 indicate that the dynamic range of enzyme assay with OD4MI CL detection is dependent on the concentration of Triton® X-100 surfactant. The dynamic range (0~0.02 U/ml) of enzyme assay in the absence of Triton® X-100 surfactant was shorter than those in the presence of Triton® X-100 surfactant. The dynamic range of enzyme assay in the presence of higher Triton® X-100 surfactant was extended up to 0.1 U/ml. The results shown in FIG. 3 indicate that Triton® X-100 surfactant is acting to interfere with the reaction between Amplex® Red reagent and $H_2O_2$ in the presence of HRP. As shown in FIG. 4, it is difficult to interact Amplex® Red reagent, which is a hydrophobic compound, with $H_2O_2$ and HRP, which are hydrophilic compounds in the presence of Triton® X-100 surfactant.

Figure 5:
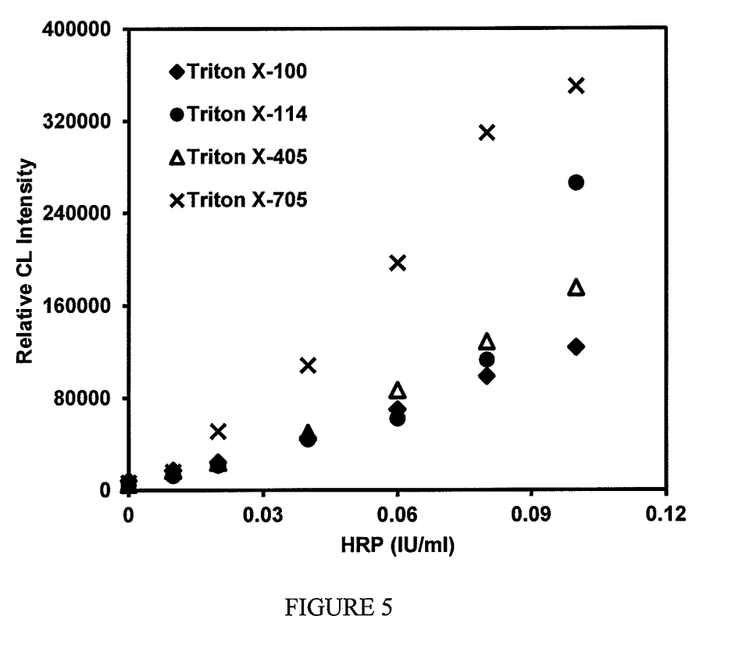
FIG. 5 shows enzyme assays in the presence of four different Triton® X surfactant derivatives (1.0%) to quantify HRP using OD4MI CL detection.

As shown in FIG. 5, all of the Triton® X surfactant derivatives are working as interference in enzyme assay to quantify HRP. The dynamic range in the presence of Triton® X-100 surfactant was wider than those in other Triton® X surfactant derivatives.

The dynamic ranges of enzyme essay for quantifying HRP in the presence of non-ionic surfactants (e.g., (2-Hydroxypropyl)-β-cyclodetrin, β-cyclodextrin, Carboxymethyl-β-cyclodextrin, Carbomethyl-β-cyclodextrin sodium salt, γ-cyclodextrin), cationic surfactants (e.g., Hexadecyltrimethylammonium bromide, Hexadecyltrimethylammonium chloride), and anionic surfactant (e.g., Sodium dodecyl sulfate) were wider than that in the absence of surfactant.

The dynamic ranges of enzyme assays with different detections (e.g., absorbance, fluorescence, luminol chemiluminescence), instead of OD4MI CL detection, for the quantification of HRP in the presence of surfactants were wider than that in the absence of surfactant. This is because all of the substrates applied for absorbance, fluorescence, and luminol chemiluminescence detection are hydrophobic compounds.

In addition, all of the surfactants are working as interference in the reaction of ALP and various substrates applied to detect absorbance, fluorescence, and chemiluminescence. This is because all of the substrates used to sense ALP are hydrophobic compounds whereas ALP is an hydrophilic enzyme.

In conclusion, a wide dynamic range to quantify hydrophilic enzyme (e.g., ellulase, cytochrome P450, esterase, β-galactosidase, β-glucosidase, β-glucuronidase, lactosidase, lipase, luciferase, protease) can be obtained in the presence of surfactant because most of the substrates applied in enzyme assays are hydrophobic compounds.

B. Quantification of AFP Using AFP Detection Antibody-HRP Conjugate and OD4MI CL Detection in the Presence of 0.1% Triton® X-100 Surfactant Preparation AccuLite® CLIA kit capable of quantifying AFP with luminol CL detection was used to develop new CLEIA method using OD4MI CL detection in the presence of 0.1% Triton® X-100 surfactant. The kit is composed of 96 strip wells coated with monoclonal AFP primary antibody, AFP detection antibody-HRP conjugate, luminol as a substrate, reaction buffer, and washing buffer.

9 different AFP serum samples (0, 9.7, 19.5, 39, 78, 156, 312, 625, and 1250 ng/ml) were used as standard samples.

2.0 μM Amplex® Red reagent and 0.2 mM $H_2O_2$ in deionized water were prepared in water containing 0.1% Triton® X-100 surfactant.

OD4MI was formed from the reaction between 5.0 μM TCPO and 10.0 μM 4-Methylimidazole (4MImH) in Ethyl acetate. 100 mM $H_2O_2$ was prepared in Isopropyl alcohol.

Procedures

12. Pipette 25 μl of AFP standard or test sample into a strip well.
13. Add 100 μl of AFP detection antibody-HRP conjugate to the strip well
14. Swirl the strip wells for 20 seconds.
15. Incubate for 30 minutes at 37° C.
16. Discard the contents of each strip wells.
17. Wash each plate with 300 μl washing buffer. Repeat four additional times.
18. Add 100 μl working solution containing 2.0 μM Amplex® Red reagent, 0.2 mM $H_2O_2$ and 0.1% Triton® X-100 surfactant in the strip well.
19. Incubate the strip-well containing Amplex® Red reagent, $H_2O_2$, and 4-Iodophenol (or 2.0 mM 4-(1,2,4-triazol-1-yl) phenol) for 15 minutes at room temperature (21~23° C.) in the dark.
20. Pipette 10 μl of working solution into the assigned test tube (12×75 mm).
21. Insert the test tube into a luminometer or the strip well into a microplate luminometer.
22. Read (integration time: 0.5 seconds) emitted CL for 0.5 seconds when OD4MI and $H_2O_2$ are added into the test tube or strip well through two dispensers.

Figure 6:
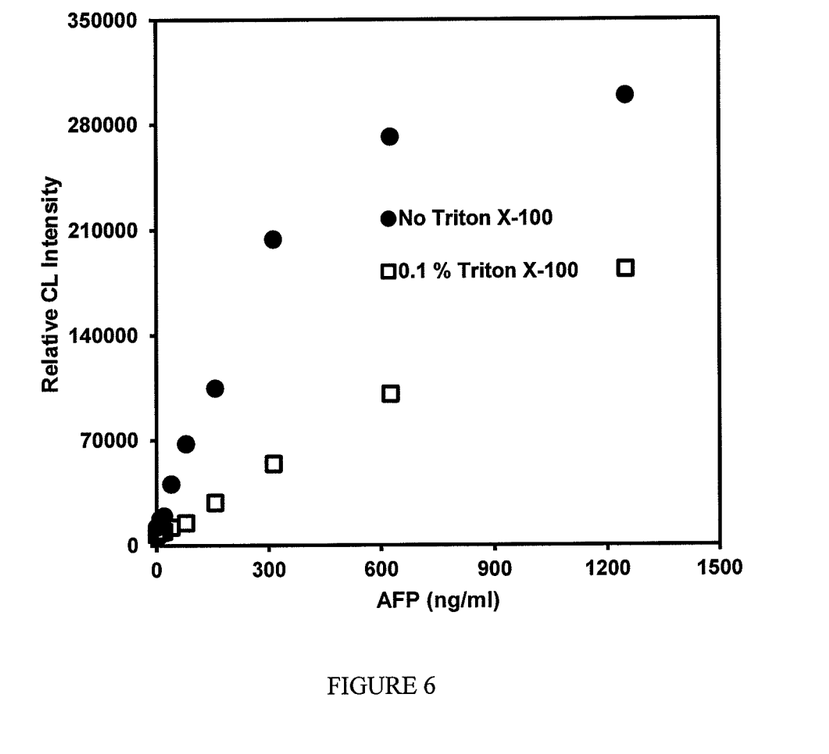
FIG. 6 shows calibration curves for the quantification of AFP using OD4MI CL detection in the absence and presence of Triton® X-100 surfactant.

As shown in FIG. 6, the linear dynamic range (0~1250 ng/ml, $R^2=0.9987$) in the presence of 0.1% Triton® X-100 surfactant was wider than that (0~313 ng/ml, $R^2=0.9962$). The sensitivity of OD4MI CLEIA for the quantification of AFP with the increase of Triton® X-100 surfactant concentration was not as good as that in the presence of 0.1% Triton® X-100 surfactant. This is because it is difficult to interact Amplex® Red reagent with HRP coated on the surface of strip-well in the presence of high concentration of Triton® X-100 surfactant.

C. Quantification of BPA Using Competitive OD4MI CL Detection in the Presence of Triton® X-100 Surfactant BPA ELISA kit was used to develop a new CLEIA method using OD4MI CL detection in the presence of Triton® X-100 surfactant.

9 different BPA samples (0.01, 0.025, 0.05, 0.1, 0.5, 1, 2.5, 5, 10 ppb) dissolved in PBS buffer (pH 7.4) were used as standard samples.

As a substrate for OD4MI CL detection, 40 μM Amplex® Red reagent containing 0.2 mM $H_2O_2$ in deionized water was prepared in the absence or presence of 0.1% Triton® X-100 surfactant.

OD4MI was formed from the reaction between 5.0 μM TCPO, and 10.0 μM 4-Methylimidazole (4MImH) in Ethyl acetate. 100 mM $H_2O_2$ was prepared in Isopropyl alcohol.

Procedure

12. Mix 60 μl of the BPA standard or test sample with 60 μl of BPA-HRP conjugate in a polypropylene well.
13. Add the mixture (100 μl) into the assigned strip wells coated with capture antibody for BPA.
14. Swirl the strip wells for 20 seconds.
15. Incubate for 30 minutes at room temperature.
16. Discard the contents of each strip well.
17. Wash each plate with 300 μl washing buffer. Repeat four additional times.
18. Add 100 μl working solution containing 40 μM Amplex® Red reagent, 0.2 mM $H_2O_2$ and 0.1% Triton® X-100 surfactant to each strip well.
19. Incubate for 15 minutes at room temperature (21~23° C.) in the dark.
20. Pipette 10 μl of working solution into the assigned test tube (12×75 mm)
21. Insert the test tube into a luminometer or the strip well into a microplate luminometer.
22. Read CL emitted when OD4MI and $H_2O_2$ are added into the test tube or strip well through two dispensers.

Figure 7:
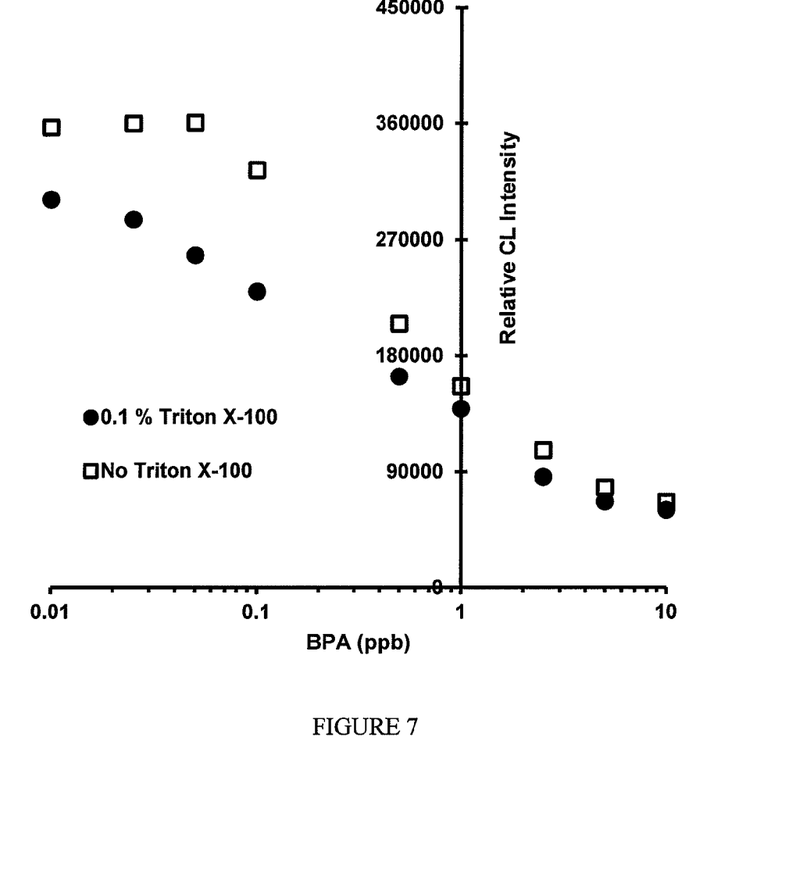
FIG. 7 is a calibration curve for the quantification of BPA using competitive OD4MI CLEIA in the absence and presence of 0.1% Triton® X-100 surfactant.

As shown in FIG. 7, the linear dynamic range (0.025~5 ppb, $R^2=0.9973$) in the presence of 0.1% Triton® X-100 surfactant was wider than that (0.1~2.5 ppb, $R^2=0.995$). The sensitivity of OD4MI CLEIA for the quantification of BPA with the increase of Triton® X-100 surfactant concentration was not as good as that in the presence of 0.1% Triton® X-100 surfactant. This is because it is difficult to interact Amplex® Red reagent with HRP coated on the surface of strip-well in the presence of high concentration of Triton® X-100 surfactant.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention. Thus, the breadth and scope of the invention should not be limited by any of the above-described exemplary embodiments.

What is claimed is:

1. A method of enhancing sensitivity of a chemiluminescent immunoassay, comprising reacting 10-Acetyl-3,7-dihydroxyphenoxazine with hydrogen peroxide in the presence of horseradish peroxidase and p-Iodophenol, wherein the chemiluminescent immunoassay further comprises 1,1'-Oxalyldi-4-methyl-imidazole (OD4MI).

* * * * *